US009267923B2

(12) United States Patent
Urey et al.

(10) Patent No.: US 9,267,923 B2
(45) Date of Patent: Feb. 23, 2016

(54) MINIATURIZED INTEGRATED MICRO ELECTRO-MECHANICAL SYSTEMS (MEMS) OPTICAL SENSOR ARRAY

(75) Inventors: Hakan Urey, Istanbul (TR); Burhanettin Erdem Alaca, Istanbul (TR); Erman Timurdogan, Izmir (TR)

(73) Assignee: KOC UNIVERSITESI, Istanbul (TR)

( * ) Notice: Subject to any disclaimer, the term of this patent is extended or adjusted under 35 U.S.C. 154(b) by 389 days.

(21) Appl. No.: 13/882,987

(22) PCT Filed: Sep. 13, 2011
(Under 37 CFR 1.47)

(86) PCT No.: PCT/IB2011/054000
§ 371 (c)(1),
(2), (4) Date: Aug. 21, 2013

(87) PCT Pub. No.: WO2012/059828
PCT Pub. Date: May 10, 2012

(65) Prior Publication Data
US 2014/0147337 A1 May 29, 2014

Related U.S. Application Data

(60) Provisional application No. 61/409,111, filed on Nov. 1, 2010, provisional application No. 61/430,871, filed on Jan. 7, 2011.

(51) Int. Cl.
*G01N 15/06* (2006.01)
*G01N 33/00* (2006.01)
*G01N 33/48* (2006.01)
*G01N 29/02* (2006.01)

(Continued)

(52) U.S. Cl.
CPC .......... *G01N 29/022* (2013.01); *G01N 29/2418* (2013.01); *G01N 33/54373* (2013.01); *G01N 2291/014* (2013.01); *G01N 2291/02466* (2013.01); *G01N 2291/0427* (2013.01)

(58) Field of Classification Search
CPC ........ G01N 15/06; G01N 33/00; G01N 33/48
USPC ............... 422/50, 68.1, 502, 503, 509, 82.05; 436/43, 174, 164
See application file for complete search history.

(56) References Cited

U.S. PATENT DOCUMENTS

2005/0043894 A1* 2/2005 Fernandez ...................... 702/19
2005/0244820 A1 11/2005 Su et al.
2005/0262943 A1 12/2005 Claydon et al.
(Continued)

OTHER PUBLICATIONS

International Search Report, mailing date May 31, 2012, for corresponding International Application No. PCT/IB2011/054000.
(Continued)

*Primary Examiner* — Brian J Sines
(74) *Attorney, Agent, or Firm* — Intellectual Property Law Group LLP

(57) ABSTRACT

This invention describes a method and apparatus for actuation and multiplexed sensing using an array of sensing elements. The invention can be used for label-free detection of biological and chemical agents in a robust, miniaturized package. The invention integrates photonics, CMOS electronics, and Micro/Nano system technologies and allows multi-analyte sensing in the same package. The preferred actuation method is using magnetic thin films and preferred sensing method is optical using interference means.

12 Claims, 19 Drawing Sheets

(51) Int. Cl.
   *G01N 29/24* (2006.01)
   *G01N 33/543* (2006.01)

(56) References Cited

U.S. PATENT DOCUMENTS

| | | |
|---|---|---|
| 2006/0191320 A1 | 8/2006 | Pinnaduwage et al. |
| 2006/0223171 A1 | 10/2006 | Craighead et al. |
| 2006/0257286 A1 | 11/2006 | Adams |
| 2008/0110247 A1 | 5/2008 | Shaw et al. |
| 2008/0146890 A1* | 6/2008 | LeBoeuf et al. .............. 600/300 |
| 2010/0217099 A1* | 8/2010 | LeBoeuf et al. .............. 600/301 |

OTHER PUBLICATIONS

Written Opinion, mailing date May 31, 2012, for corresponding International Application No. PCT/IB2011/054000.

* cited by examiner

MINIATURIZED INTEGRATED MICRO ELECTRO-MECHANICAL SYSTEMS (MEMS) OPTICAL SENSOR ARRAY

CROSS-REFERENCE TO RELATED APPLICATIONS

This application is a U.S. National Phase application, under 35 U.S.C. §371, of International Application no. PCT/IB2011/054000, with an international filing date of Sep. 13, 2011 and claims the benefit of U.S. Provisional Patent Application Ser. Nos. 61/409,111, filed on Nov. 1, 2010 and 61/430,871 filed on Jan. 7, 2011, all of which are entirely incorporated herein by reference in their entireties.

FIELD OF THE INVENTION

The present invention relates to a Miniaturized Integrated Micro Electo-Mechanical Systems Optical Sensor Array (MIMOSA) including micro electromechanical systems (also called "MEMS") and more preferably to sensor arrays using moving mechanical surfaces and most preferably to label-free biological sensing.

BACKGROUND

In the area of sensing, vibrating mechanical structures, for example, microcantilever arrays find various applications based on advantages such as lower detection limits due to miniaturization, the ability of shape optimization of cantilevers, the ability to selectively place functionalized regions on the these cantilevers (also interchangeably called "microcantilevers"), and the possibility of working on large arrays which can be integrated with optics and electronics.

Some of the disadvantages of these currently known types of sensors are; that they require electrical connections (also called electrical conductors) to couple the sensor to a detector, limited optical detection options, limitations to liquid or gas phase detection, sensors that use frail readout components (for example, Doppler vibrometry), readouts that can be affected by refractive index variations due to monitoring of the deflection, sensors with no immunity against environmental noise, and the inability to heat the cantilever/samples during sensing. Further, it is believed that current alternatives to parallel sensing are limited to laboratory use only. It is therefore desirable to have a fieldable, label-free demonstrator, which is missing due to the lack of various components including a suitable readout mechanism that can be utilized in an array setting, a package that would protect functionalized surfaces during shelf life, which usually requires handling of liquids, and an integrated approach that would allow disposal of certain components, whereas others remain for the next use (for example, disposable cartridges containing the MEMS sensor array).

One objective of this invention is to enable a MEMS sensor array having a sensor array that is miniaturized, highly selective, highly sensitive, parallel, label-free and/or portable. Such a sensor array will provide a valuable tool for point-of-care diagnostics and chemical sensing with its capabilities of a single analyte or a multianalyte screening and data processing. It is a further objective of these sensor arrays to increase sensitivity and specificity to possibly increase the likelihood of early diagnosis as well as the suitability of treatment assistance, such as dosage advice. It is envisioned that this may lead to increased effectiveness of doctor-patient interaction and personalized guidance. It is believed that such systems that meet the demands of parallel, label-free, and highly selective sensing do not exist today as microsystem technologies and readout methods cannot meet expectations for various reasons including: robustness issues associated with functional surfaces and the lack of a truly integrated, array-compatible readout techniques. Alternatively, it is believed that microarray technologies can offer parallel and selective detection, but are not fieldable as they require expertise to run and maintain and require expensive infrastructure due to complex labeling and sensing methods. While many fieldable applications, such as pregnancy test kits or the glucose sensor exist, these applications are limited to one kind of species and lack parallel detection capability.

the sensor array platform is highly innovative and versatile and has inspired by the novel uses. For example, for the point-of-care diagnostics applications it is envisioned that a microsystem-based parallel sensor array (2 to 64 channels and more), can be used for various species for shifts in resonance frequency of an array of cantilevers will be monitored as an indication of mass accumulation. In this example, detection of frequency shifts will be carried out through a novel integrated optoelectronic chip. Sensitivity in the range of 0.1 to 1000 ng/ml with better than 25% reproducibility is aimed.

Additionally, possible uses of this invention include liquid phase detection of disease from body fluids (e.g., blood, serum, urine, or saliva), gas phase detection as an artificial nose sensor serving as air pollutants detector airborne disease diagnosis tool, warfare pathogens detector and explosives trace detector. It is envisioned that one can use the apparatus to detect substances that are characterized with low vapor pressure and hence are hard to detect; for example, to identify explosive traces, possibly with a potential sensitivities capable of sensing masses on the order of femtograms. Further refinements, such as a pre-concentrator increase the vapor pressure, may be proposed to further increase sensitivities. Another novel aspect of the invention is identifying the material not only by its simple adsorption signature, but also through adsorption/desorption isotherms that can allow identifying, with higher accuracy, the substance or the components of a mixture. Additionally, it is believed that in an aqueous medium, the invention will allow parallel, fast, real-time monitoring of a large number of analytes (e.g., proteins, pathogens, and DNA strands) without any need for labeling, and, therefore, be ideal for the targets screening in drug discovery process, or as a promising alternative to current DNA and protein micro array chips. Using such a label-free apparatus may decrease the number of preparation stages and shorten diagnosis time. It is proposed that one can investigate DNA sequences, successful results will be the positive detection of various mutations in human DNA (e.g., sickle cell anemia, -thallesemia) in parallel.

This invention demonstrates a highly parallel label-free detection of (bio/chem) agents in a robust, miniaturized package using multiple disciplines including integrated photonics, VLSI, and Micro/Nano system technologies to develop a versatile sensor array with breakthrough performance.

each sensor is typically located on a MEMS sensor array operates by monitoring the resonant frequency of the vibrating mechanical structures (also called cantilevers or microcantilevers). Output of a sensor is the change in resonant frequency in response to accumulated mass on the cantilever due to a specific binding event. The array of cantilevers may be actuated by an actuating means; for example, electromagnetic force means; piezoelectric force; electric force; electrostatic force means and combinations thereof. The most preferred actuating means is a single electro-coil that carries a superposed drive current waveform. Preferably Optical feedback from a mechanism to sense light coupled with each sensor is used for detection of specific binding events and also for closed-loop control of the cantilevers at resonance. More preferably, damping can be tuned by closed-loop control electronics allowing sharp resonance peaks (high-Q) even in liquid media. In a preferred embodiment, frequency resolution is inherently higher compared to other read-out techniques such as the piezoresistive or capacitive methods.

preferably, the MEMS chip contains the functionalization layer on magnetic structural layer (for example, Nickel). More preferably, the location on the cantilever of the functionalized layer can be chosen to maximize the resonant frequency shift per added unit mass. In a preferred embodiment, the novel structure of the cantilevers includes a diffraction grating in the form of simple slits and/or heating elements. The MEMS sensor array (also called a MEMS chip) is preferably envisioned to be disposable and replaceable in future products; for example, as a disposable cartridge containing a MEMS sensor array to be coupled with a detector apparatus containing an actuating means (also sometimes called an actuator). This preferred embodiment would leave the actuator and electronics layers intact for reuse. Preferably, the MEMS chip is a passive component with no electronic link (also called an electrical conductor) to the detector apparatus. In this preferred embodiment this will facilitate work in fluidic environments, since less isolation, coupling, and stiction issues need to be considered. Furthermore, the preferred embodiment includes the integration of electronics and optics coupled with a passive component to provide ease and flexibility of use compared to a direct integration of the MEMS layer with IC detection apparatus. Finally in a preferred embodiment, magnetic actuation can be carried out remotely through an external electromagnetic coil on the MEMS chip. It is believed that sensitivity levels achieved in mass measurements will directly be reflected by detection sensitivity of the analytes of interest. Additionally, the type of surface functionalization utilized on the cantilever surfaces will determine the field of application, e.g., Human Kappa Opioid receptor (HKOR) is utilized for the detection of narcotics. In a preferred embodiment it is believed that a minimum mass detection limit of 500 femtograms or less may be achieved through discrete optics, electronics, and an electromagnet. Preferably, integration of discrete components and further miniaturization will substantially improve the minimum detection limit, sensitivity, parallelism, and robustness of the apparatus and will meet the challenges of label-free and parallel detection in a portable device.

SUMMARY it is an object of the present invention to provide [will be filled in when the claims are finalized].

the novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

Figure 1:
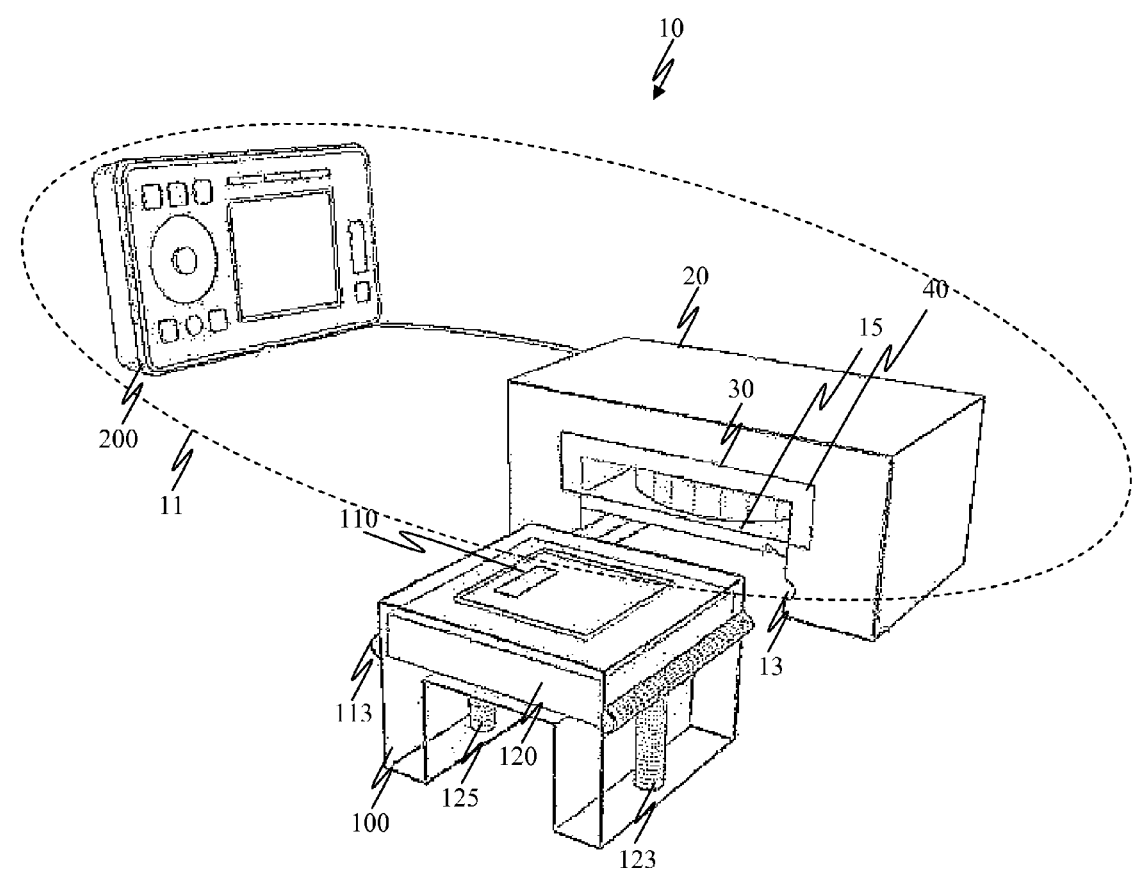
FIG. 1 is a diagrammatic view of a preferred embodiment of a system concept for integrated readout illustrating operation for liquid-phase or gas-phase sensing.

DESCRIPTION OF PREFERRED EMBODIMENTS in a preferred embodiment the key areas of the system can be listed as follows: (1) A detector chip preferably including a silicon based novel integrated optoelectronic chip utilizing die-bonded laser diode array (1D VCSEL array), photodetectors, and CMOS readout electronics with wafer thinning and Si via technology; (2) A MEMS sensor array 110 (also called a MEMS chip) with micro/nano resonant cantilevers with integrated grating structures, heating elements and, remote electromagnetic actuator for a disposable chip; (3) 3D integration of integrated optoelectronics chip and MEMS chip with hybrid-stacking; (4) Functionalization of MEMS cantilevers with different specific recognition molecules (proteins, oligonucleotides, chemical assemblies) with focused immobilization methods addressing only one individual cantilever from the array; (5) Demonstration of parallel sensor array operation (from 2 up to 64 parallel channels) for highly selective and accurate recognition of chemical and biological agents.

in a preferred embodiment involves the design and fabrication of the MEMS chip on SOI wafer with nickel cantilevers. The idea of an integrated diffraction grating has already been demonstrated to provide extremely high-resolution displacement detection (with demonstrated sub-angstrom average detection limit) for Atomic Force Microscope (AFM) and other applications with simple fabrication and good immunity to environmental noise. In a preferred embodiment microcantilevers can be replaced by membrane devices and in a preferred operation mode, cantilevers or membranes can be coupled with an actuator to adjust the gap to selectively tune the responsivity.

a preferred embodiment also involves the design and fabrication of a detection apparatus comprising a detection chip and a control electronics that functions independently of the MEMS layer. Preferably the detection apparatus is a universal read-out with no physical connection or electrical conductors to MEMS chip such that there is no electrical connection for electrons to flow from the detector chip or detector apparatus to the MEMS sensor array 110 and vice-versa. While VCSEL array technology is commercially available, it cannot be placed on the same side with the photodetectors due to high packing density in the parallel sensor array and can be vertically integrated with flipchip bonding. Silicon via technology developed for 3D hybrid chip stacking will be utilized to channel the VCSEL or other laser light onto MEMS chip. The preferably envisioned platform is versatile and can be utilized for optical interconnects and other photonics applications.

Preferably the detection apparatus includes a control electronics involving closed loop control of MEMS cantilevers using the detector chip with optical feedback at resonance, noise cancellation, and precise frequency measurement to detect dynamic changes. The detecting apparatus is preferably designed to be able to handle vapour phase and aqueous phase samples. The detector chip, preferably an optoelectronic chip, and the disposable MEMS layer are preferably aligned with good precision. Preferably this can be realized through mechanical guides machined in the package, and more preferably active alignment can be used to achieve few microns precision.

Preferably, the individual components of the sensor array can each be optimally designed and manufactured and various noise reduction techniques can be implemented to achieve sensitivities approaching the fundamental limits. Developing compact, highly functional, portable and disposable sensors for bio-sensing, gas sensing, thermal sensing using an absorption area and thermal isolation legs, and spectroscopic devices using grating and selective absorbing materials with this sensor array technology. Hence, realization of the proposed ideas will contribute to a personal health system through multi-analyte diagnostics capability, increased effectiveness in doctor-patient interaction, early detection of diseases and their recurrence including cancer, and detection of hazardous substances for security.

To increase the selectivity, it is preferable to perform multi-modal detection by simultaneously employing additional measurements. In addition to resonant frequency shift, one can monitor the following:

Deflection amount
  Perform localized heating on the cantilever to bring about the differences in thermal properties of materials and molecules and obtain certain phase diagrams, forced adsorption/desorption
  Perform spectral measurement. Spectral measurement can be aided by the fact that the cantilevers are moving to achieve dynamic effects.

Explosive agent detection and DNA mutation detection are exemplary demonstrators of possible use. The sensing surface of individual cantilevers should be appropriately activated (self-assembled monolayer, hydrophilic polymer coating) for covalent immobilization of recognition molecules. In one embodiment, precise addressing of reagent solutions can be achieved using ink-jet deposition system, dip coating, microspotting, or using microfluidic channels for each analyte; alternatively, photoactivation-based chemical reactions will be employed providing reactive groups only in the light-activated surface zones. It is envisioned that model (bio) ligands for covalent immobilization can include antibodies (immunosensing), oligonucleotide probes (hybridization assays) and chemical assemblies (nanotubes, nanoparticles, supermolecular complexes, lipid bilayers). It is believed that surface density of binding sites will be determined using enzyme labeling, fluorescent microscopic imaging and/or atomic force microscopy). Further exemplary embodiments are described below.

FIG. 1 show a preferable disposable package 10 concepts and illustrates that there may be no electrical conductors (also called electrical connections) to the disposable cartridge 100. Likewise, microfluidics handling can be integrated (e.g., simple filtration can be used) with the disposable package 10 to separate serum from a drop of blood and then drive the serum onto the cantilevers for measurement. The preferable disposable package 10 shown in FIG. 1 includes a detector apparatus 11 having a detector chip 20 (also called "a reusable sensor head 20") having an actuating means 30 preferably an electromagnet used for AC (alternating current) actuation and, preferably, a permanent magnet 40 for magnetic field enhancement. The disposable package 10 shown in FIG. 1 also preferably includes a disposable cartridge 100 having mechanical guides 113 and including a MEMS sensor array 110 coupled to a fluid contacting system 115 preferably comprising a fluid chamber 120 (also sometimes called "a reaction chamber"), a fluid inlet 123 coupled to the fluid chamber 120 and a fluid outlet 125 also coupled to the fluid chamber 120. In some instance the fluid inlet 123 and the fluid outlet 125 may occur through the same space designated as a fluid inlet/outlet 127. The preferable reusable sensor head 20 also includes a mechanism to sense light which preferably is an optoelectronic readout 15 to measure the MEMS sensor array 110. Further, the preferable detector apparatus of the disposable package 10 shown in FIG. 1 also preferably includes a control electronics and user interface 200 coupled to the reusable sensor head 20.

Figure 2:
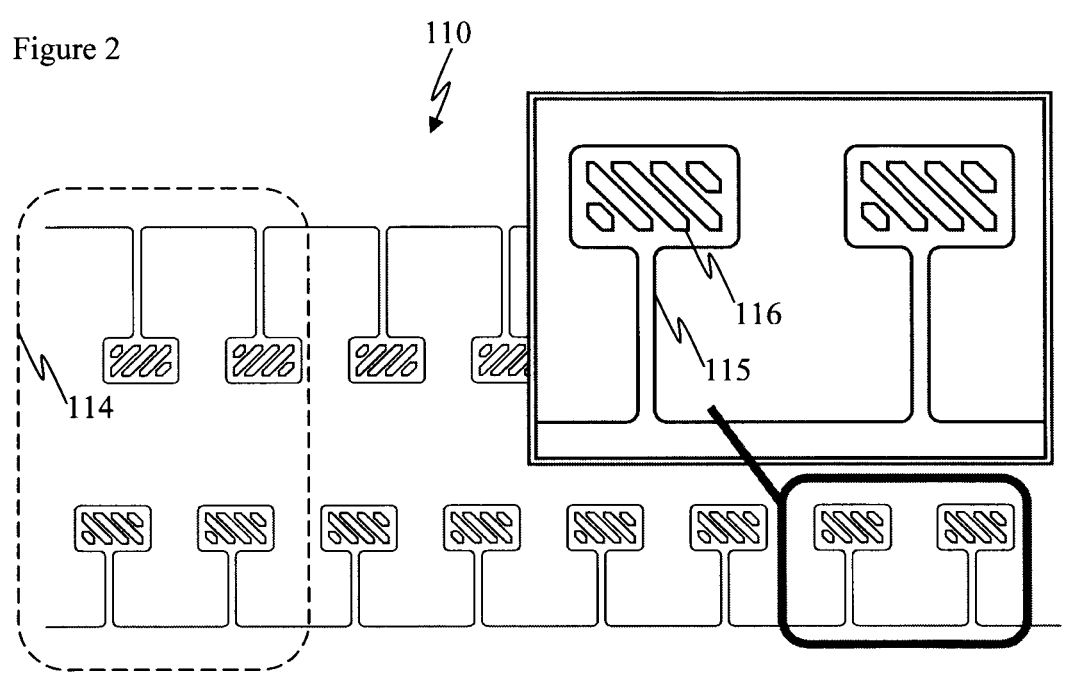
FIG. 2 is a top view diagram of one preferred embodiment of one microcantilever array including embedded diffraction gratings and including an enlarged view thereof.

FIG. 2 shows a top view of one preferred embodiment of one microcantilever array 114 including embedded diffraction gratings 116.

Figure 3:
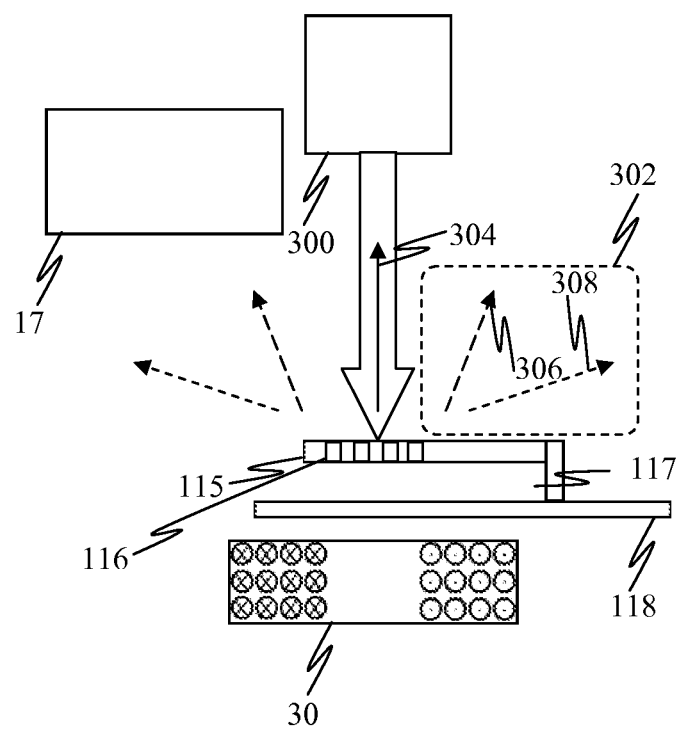
FIG. 3 is a diagrammatic side view of one preferred embodiment of the invention including details of the optical readout.

FIG. 3 shows details of a preferred embodiment of an optical readout diagrammatically includes a cantilever 115 having grating 116 coupled to a substrate 118 to form a gap 117. An actuating means 30, preferably an electromagnet and most preferably an electro-coil as shown, is placed below the substrate 118 which may cause the cantilever 115 to vibrate at certain frequencies. Also shown is a preferable laser 300 which couples to the grating 116 and forms refracted orders 302: $0^{th}$ order refraction 305, $1^{st}$ order refraction 306 and $3^{rd}$ order refraction 308 as preferably shown. The refracted orders 302 can be coupled to a photodiode 17 for detection. The signal output from the photodiode 17 is represented by diffracted order intensities in (b) for the $0^{th}$ order refraction and the $1^{st}$ order refraction.

Figure 4:
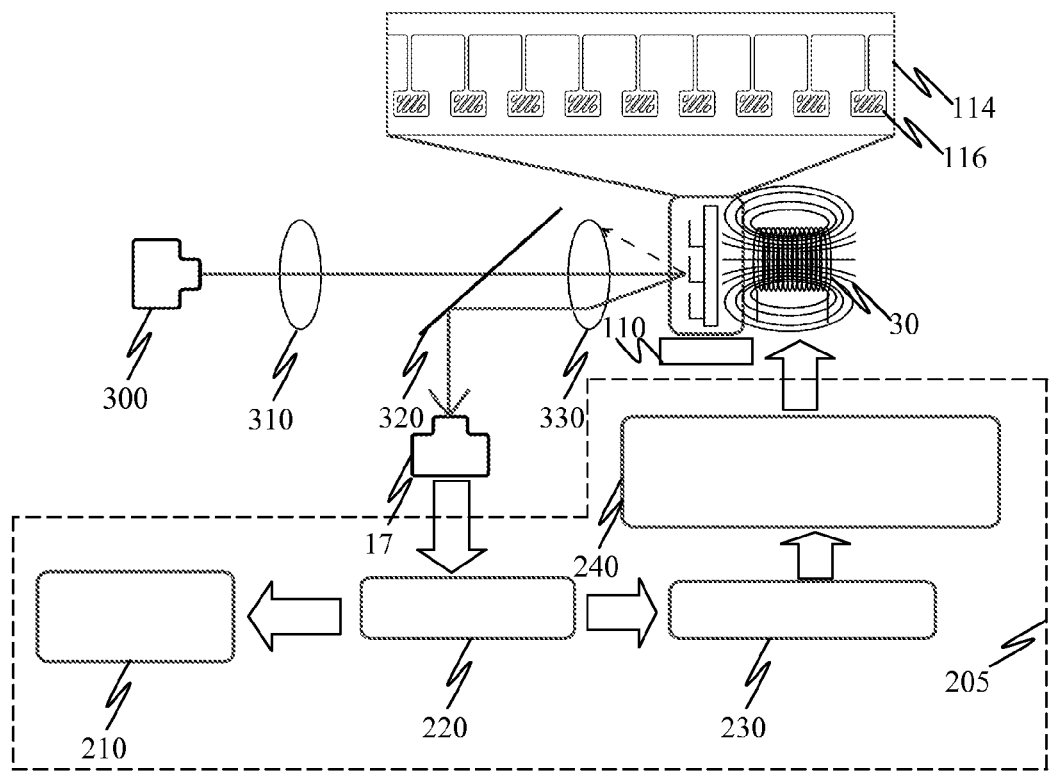
FIG. 4 is a diagrammatic view of one preferred embodiment of the invention illustrating the details of the closed-loop electronics system and the optical readout system, where the resonant frequency of the microcantilever is the desired sensor output.

FIG. 4 illustrates the details of one preferred embodiment of a closed-loop electronics system 205 (may be part of the control electronics and user interface shown in FIG. 1) and the optical readout system 15 (may also be known as the optoelectronic readout; for example as in FIG. 1), where the resonant frequency of the microcantilever 115 is the desired sensor output. In this preferred embodiment, the optical readout system 15 includes a laser 300, preferably a red laser diode, a first lens 310, a beam splitter 320 a second lens 330 and a photodetector 17 wherein the beam splitter can interact with an individual grating 116 of the cantilever 115 or in parallel with gratings of the microcantilever array 114. In this preferred embodiment, the closed-loop electronics system 205 includes a preamplifier coupled to the photodetector 17 output, a frequency counter 210 coupled to the output of a preamplifier 220, a phase shifter 230 coupled to the output of a preamplifier 220 and a feed-back generator coupled to the phase shifter 230 and an electromagnet 30 that couples to the MEMS sensor array 110. Preferably the feedback for self-excitation is in the frequency range of 20 kHz to 800 kHz. This sensor system can simultaneously monitor an array of cantilevers using one actuator (such as piezoelectric or electromagnetic or electrostatic) and one photodetector and one set of electronics. In a preferred embodiment amplifier and the phase shifter need to be broadband in order to support a range of distinct resonant frequencies within the cantilever array. In a preferred embodiment MEMS cantilevers can be illuminated with a laser line or with a laser spot array. Reflected light from the substrate and the sensor surface interfere and create diffraction orders. 1st diffraction order is monitored to avoid large bias in the 0th order direct reflection beam. There is a nonlinear relation between the cantilever deflection and the photodetector intensity, which is important for making an array of oscillators. Responsivity of each cantilever depends on the gap underneath each cantilever but the frequency of oscillation is not affected by the gap or other factors such as refractive index variations or vibrations. Oscillations start with Brownian motion and amplified by the control system and lock at resonant frequency of each cantilever, which can be precisely monitored using frequency counters. Multiple cantilevers can be monitored real-time with one detector and one actuator. In SSA mode, frequency peaks corresponding to microcantilevers are very sharp compared to the open-loop response using frequency sweeping. Sharpness of the resonance is only limited by the measurement settings of the spectrum analyzer but there are still limits about the frequency separation of cantilevers that are monitored together. Frequency bandwidth of one of the cantilevers in a preferred embodiment was measured as 1 Hz in self-oscillation mode while it is resonant frequency was 92 KHz. In the experiment, multiple cantilever operation was demonstrated (7 cantilevers in one experiment) in parallel. The level of multiplexing achieved using a single set of electronics, actuator, and photodetector is unique. The method allows dense array of sensors on a small chip and can make measurement using small sample volumes. Therefore, it can open up new horizons for parallel and real time sensing and imaging applications such as multiplexed diagnostics with small sample volumes or parallel AFM or other parallel read/write head for data storage and imaging applications.

Figure 5:
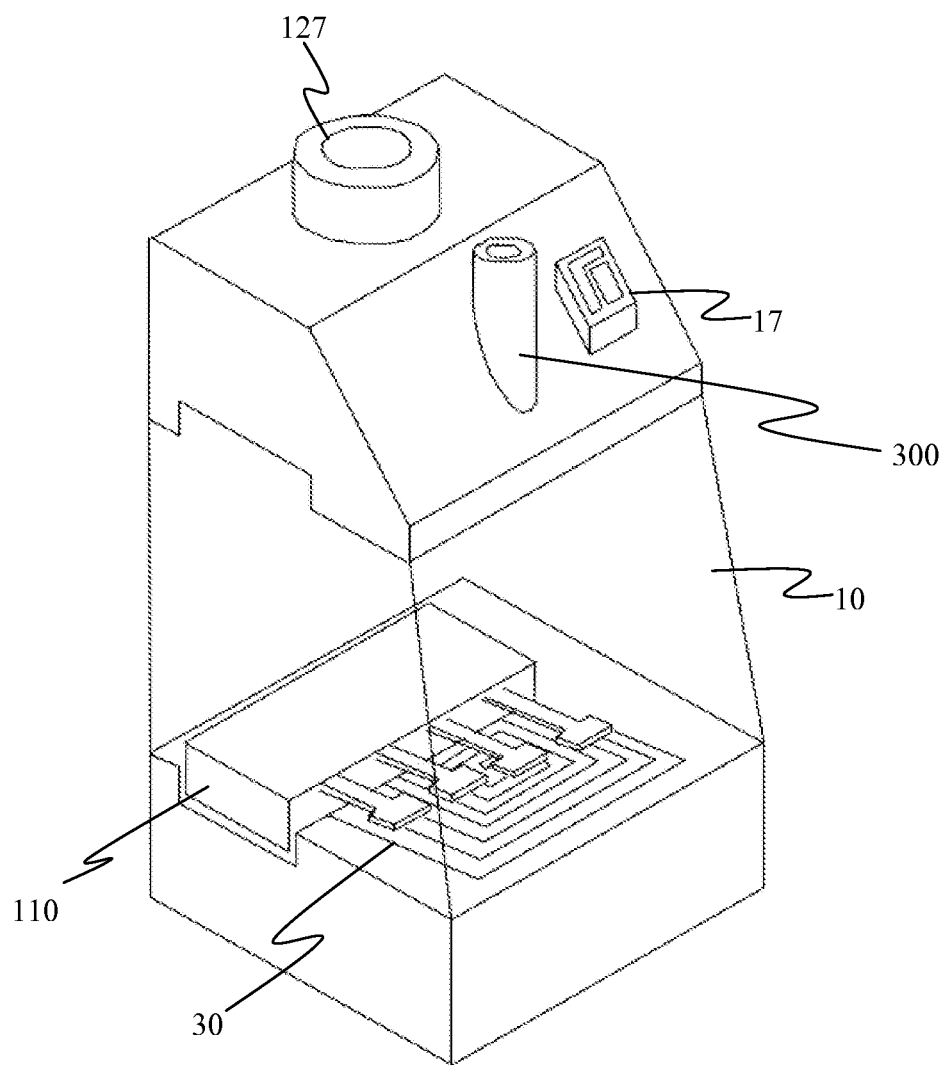
FIG. 5 is a diagrammatic view of a preferred embodiment of a system concept for multiplexed optical readout using single laser and single detector.

As shown in FIG. 5, free space optics can be used to distribute light from one source to many vibrating mechanical structure 115. Preferably, a single electro-coil can actuate and control many vibrating mechanical structure 115 (also called cantilevers) of a MEMS sensor array 110. Preferably, the single magnet coil shown can activate different weight cantilevers 115 to provide have different detection limits or species. This figure also shows one preferred embodiment for an optical readout using free space optics where a laser 300 couples to microcantilever 115 having a grating 116 and refracted orders 302 are detected by a single photodiode 17; however, one or more lenses (not shown) may optionally be used. Preferably, a single electro-coil 30 can be used to actuate multiple cantilevers by using frequency multiplexing. More preferably, the laser 300 may be used as a source of heating for the cantilevers 115.

Figure 6:
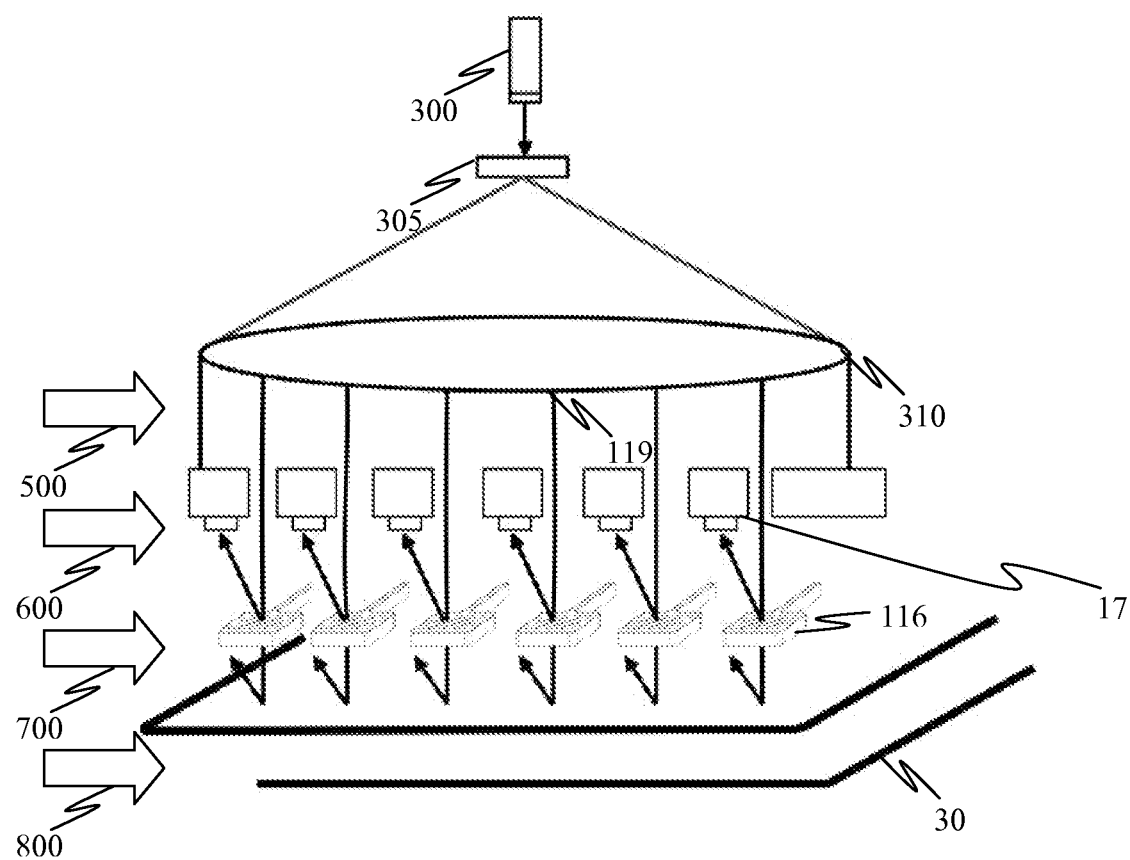
FIG. 6 is a diagrammatic view of a preferred embodiment of a concept illustrating different layers including one laser illuminates plurality of sensors in the array and the output of each sensor is coupled to at least one photodetector (PD).
Figure 7:
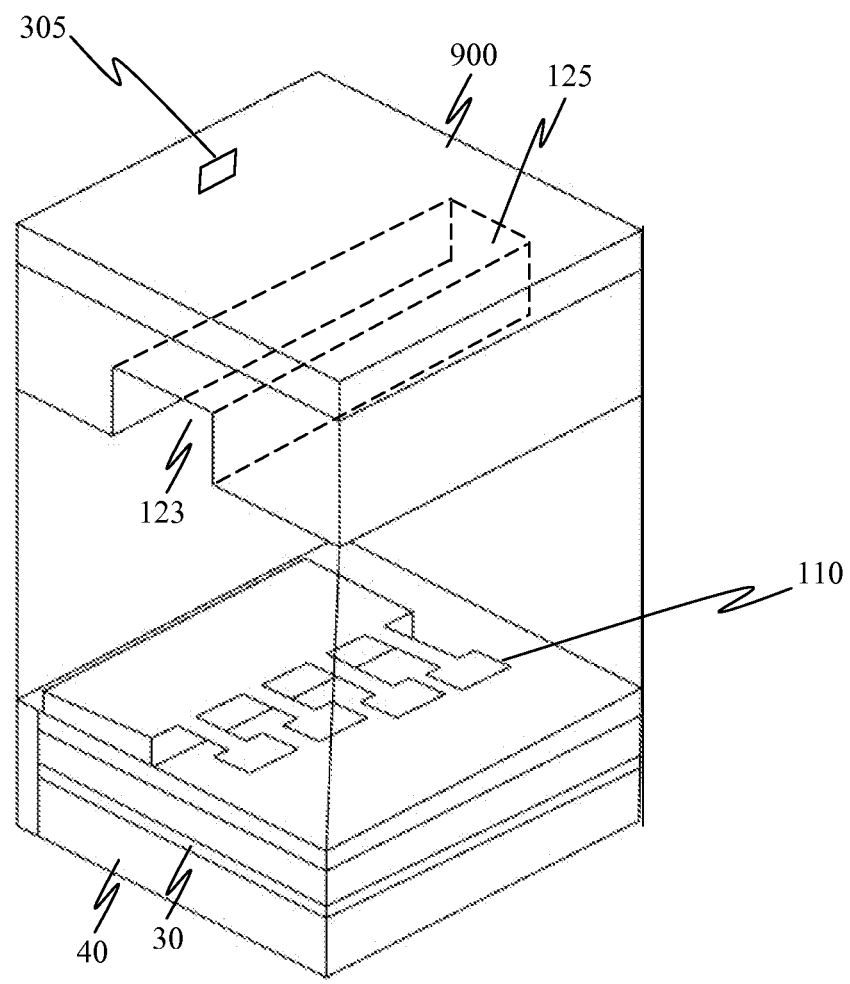
FIG. 7 is a diagrammatic view of a preferred embodiment of a concept illustrating different layers including Free space optics is replaced with a waveguide layer for light distribution to each channel, waveguides can be formed at the front side of the optoelectronic (OE) chip or at the back side.
Figure 8:
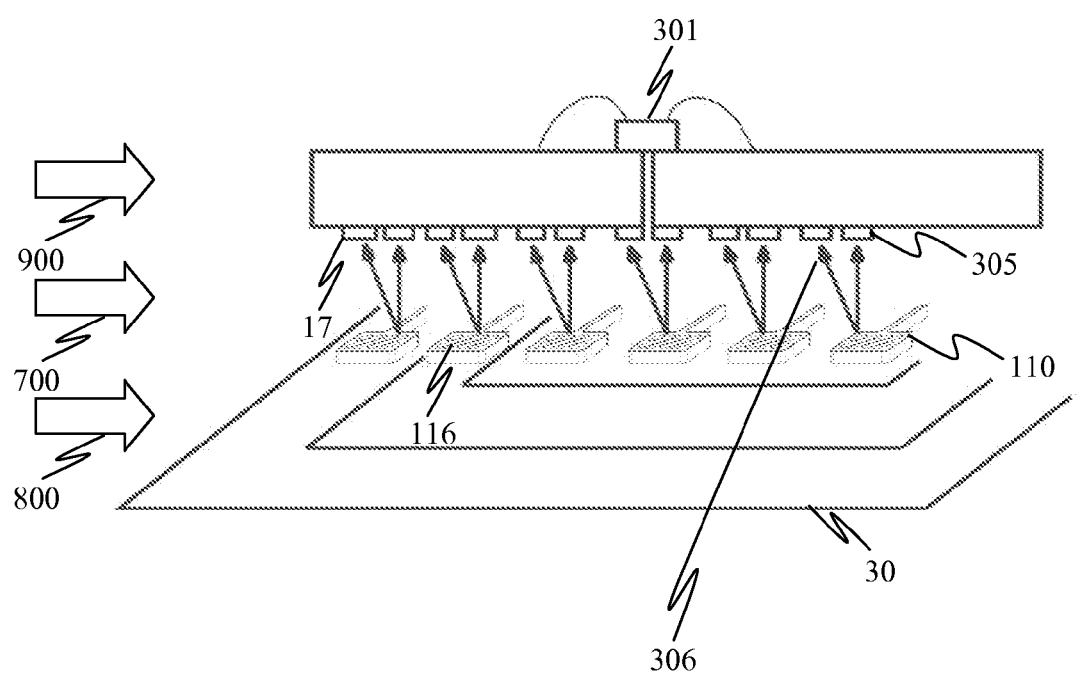
FIG. 8 is a diagrammatic view of a preferred embodiment of a concept illustrating different layers including VCSEL light illuminate each cantilever of the invention (VCSEL: vertical cavity surface emitting laser)
Figure 9:
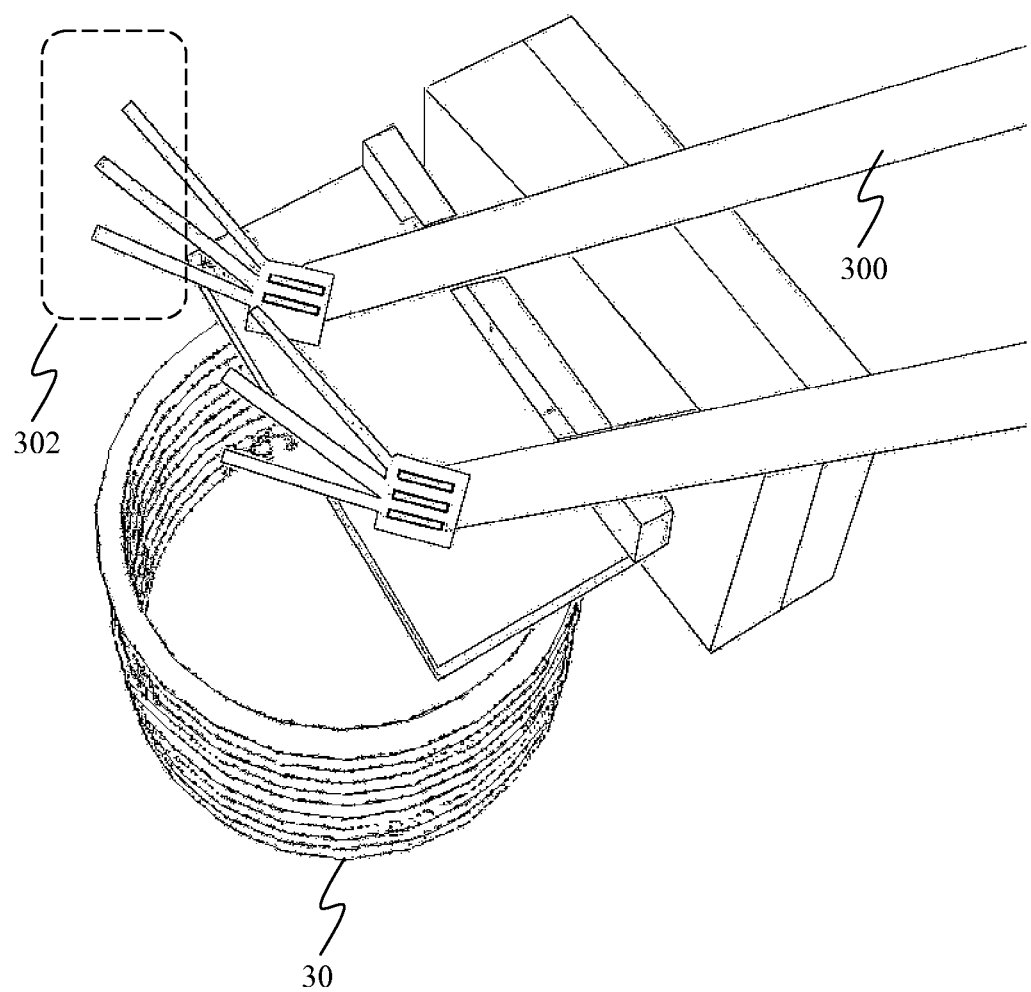
FIG. 9 is a diagrammatic view of a preferred embodiment showing the details of the MEMS chip and the optoelectronic chip including magnetic actuation and diffraction grating readout of 2 cantilevers are illustrated. Incident beam and reflected 3 diffraction orders are illustrated.
Figure 10:
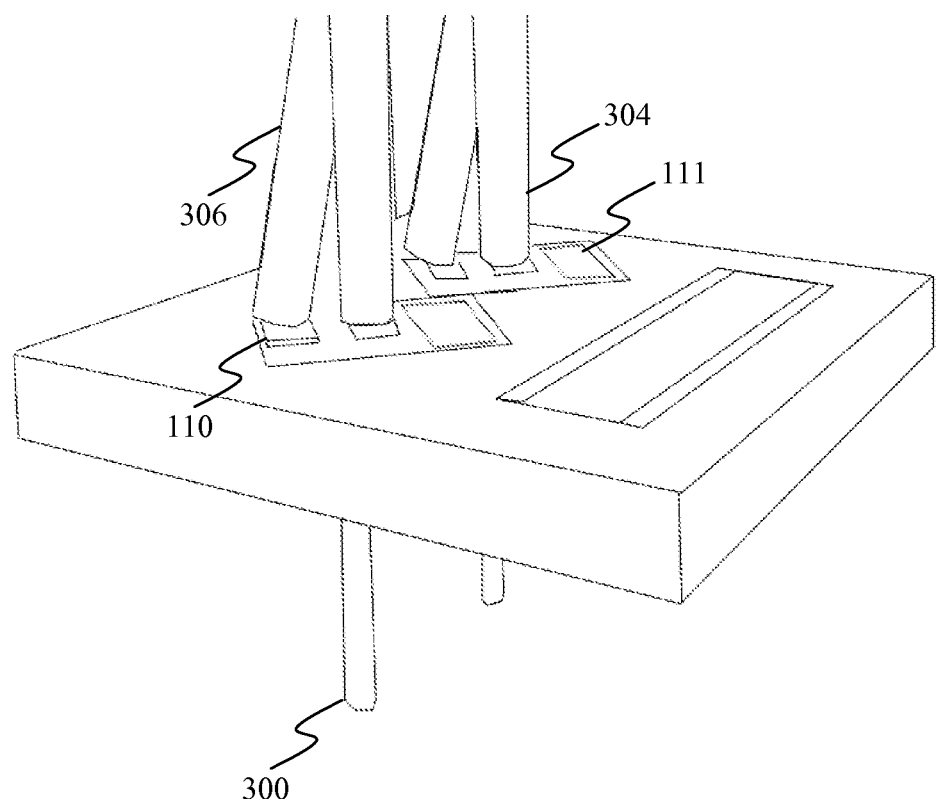
FIG. 10 is a diagrammatic view of a preferred embodiment showing the details of the MEMS chip and the optoelectronic chip including the optoelectronic readout where Light from a laser source goes through silicon via. The two diffraction orders ($0^{th}$ and $1^{st}$ orders) are collected by 2 photodetectors. Transimpedance amplifiers for each Photodetector (PD) is illustrated adjacent to each detector. Other CMOS circuitry can perform other analog and digital functions such as noise cancellation, digitization, etc.
Figure 11:
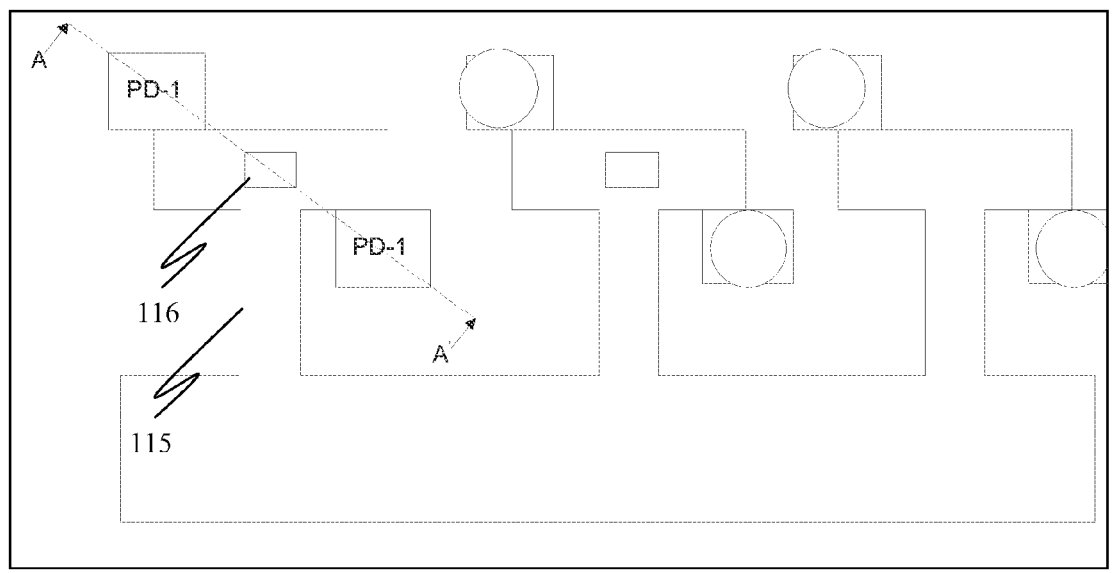
FIG. 11 is a diagrammatic view of a preferred embodiment showing the details of layers for the integrated readout including a bottom view of different layers and each sensor illustrates layers at different chips.
Figure 12:
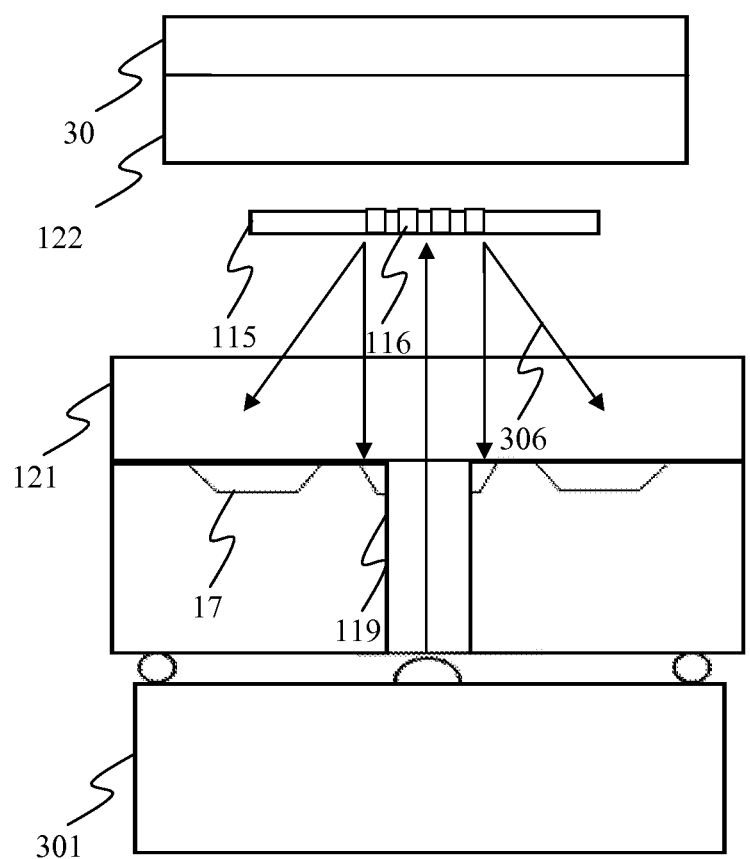
FIG. 12 is a diagrammatic view of a preferred embodiment showing the details of layers for the integrated readout including AA' cross-sectional view of layers. VCSEL and optoelectronic layers are integrated using flipchip bonding. MEMS layer has no electrical interconnects and located on the disposable chip and aligned using by using mechanical guides in the structure.
Figure 13:
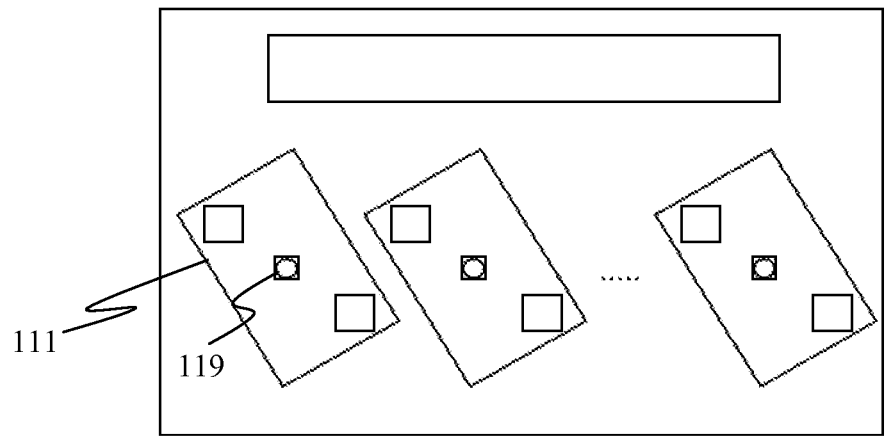
FIG. 13 is a diagrammatic view of a preferred embodiment showing the details of layers for the integrated readout including View of the optoelectronic layer with an area dedicated to CMOS readout IC. Via opening and wafer thinning are post-CMOS processes.
Figure 14:
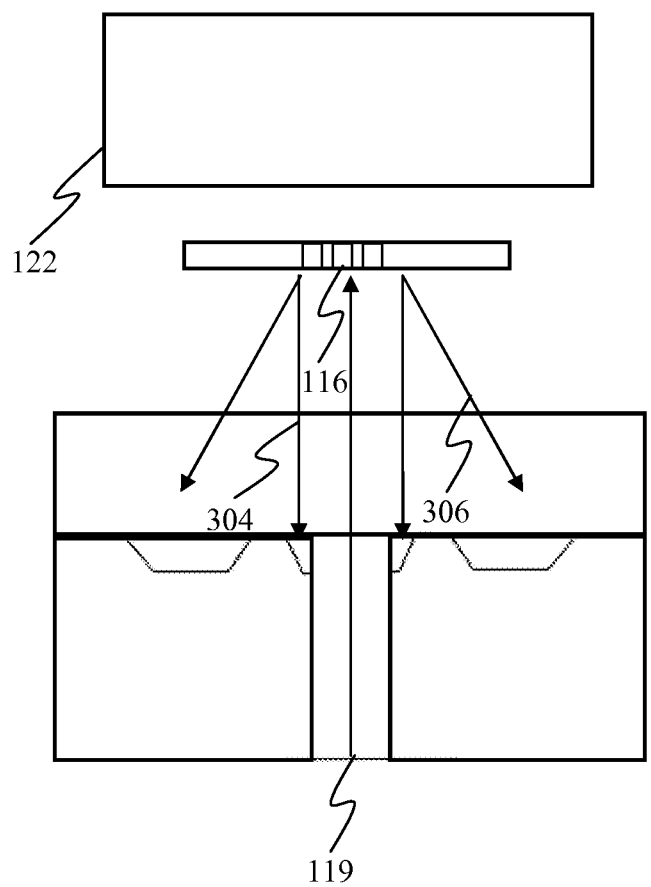
FIG. 14 is a diagrammatic view of a preferred embodiment showing the integrated grating readout without using lenses proof of concept numerical simulations.

FIGS. 6, 7 and 8 illustrate the integration of detector apparatus (also called optoelectronic readout) with MEMS sensor array 110 without using free-space optical elements such as lenses and imaging. In this preferred embodiment, there is at least one photodetector coupled with each vibrating MEMS cantilever. This preferred embodiment shows the following elements: the optics 500, the electronics 600, the mechanics 700, including the vibrating mechanical structure 115 (and which may also be a MEMS sensor array 110), and the activating means 800 schematically. Alternatively, the electronics 600 and optics may be combined to form an optoelectronic layer 900 (which may also be the optoelectronic detector). In a most preferred embodiment, all of the elements 500, 600, 700 and 800 may be combined into a single unit. The light from the laser 300 is allowed to pass through a via 119 made on the CMOS integrated circuit with post-processing. In this preferred general approach one light source is used to illuminate and array of cantilevers 114. Preferably, the laser 300 shown in this figure also shows further integration with VCSEL 301 (vertical-cavity surface-emitting laser) or a laser diode array. In this preferred embodiment, having a separate laser light source coupled with each cantilever 115 allows for laser modulation, laser heating, or other changes to be performed in real-time selectively to different selected cantilevers. Preferably, the actuation is performed using one single magnetic coil 30 that energizes an array of cantilevers 114. Preferably detection is accomplished by reimaging with a lens system onto a detector array. One or many photodetectors can be dedicated to each cantilever.

FIGS. 9-13 are a preferred embodiment diagrammatically showing the details of the MEMS chip and the optoelectronic chip for (a) a Magnetic actuation and diffraction grating readout of 2 cantilevers (Incident laser beam and refracted orders 302 are illustrated) and (b) an optoelectronic readout where light from a laser 300 goes through silicon via 119 and two diffraction orders ($0^{th}$ and $1^{st}$ orders) are collected by 2 photodetectors. Preferably, transimpedance amplifiers 111 can be used for each photodetector as illustrated adjacent to each detector. Preferably, other CMOS (complementary metal-oxide-semiconductor) circuitry can perform other analog and digital functions such as noise cancellation, digitization, etc.

Figure 15:
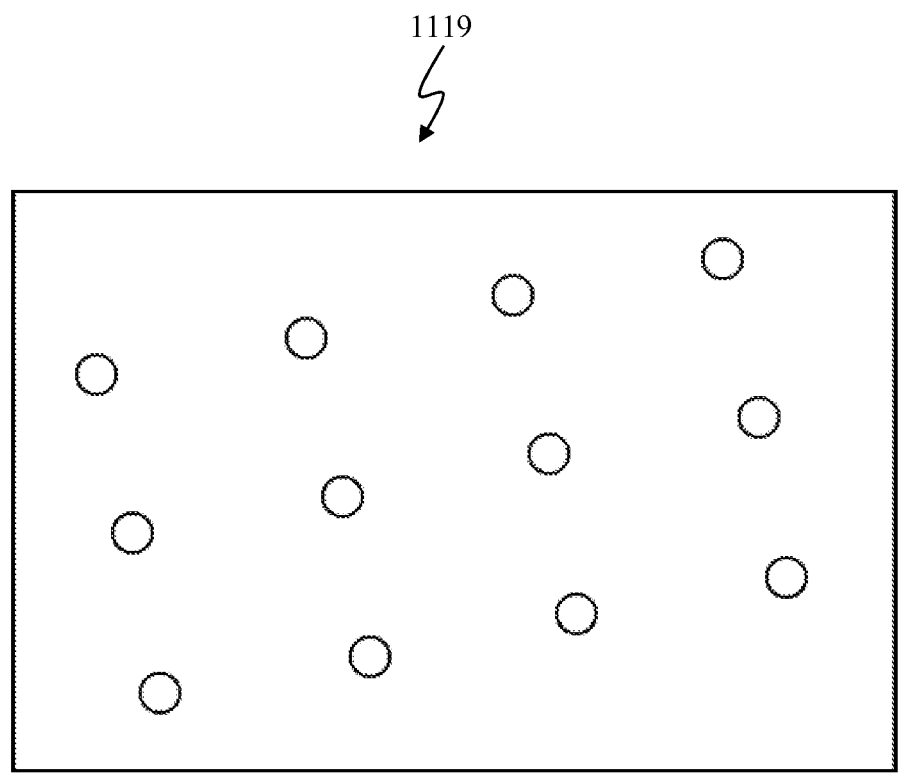
FIG. 15 are views of a preferred embodiments showing (left): SEM pictures of the array of holes on thinned Silicon wafer suitable for integrated grating readout and (right): Microscope pictures of holes on Silicon wafer and a diffraction grating placed underneath the thinned Silicon wafer.
Figure 16:
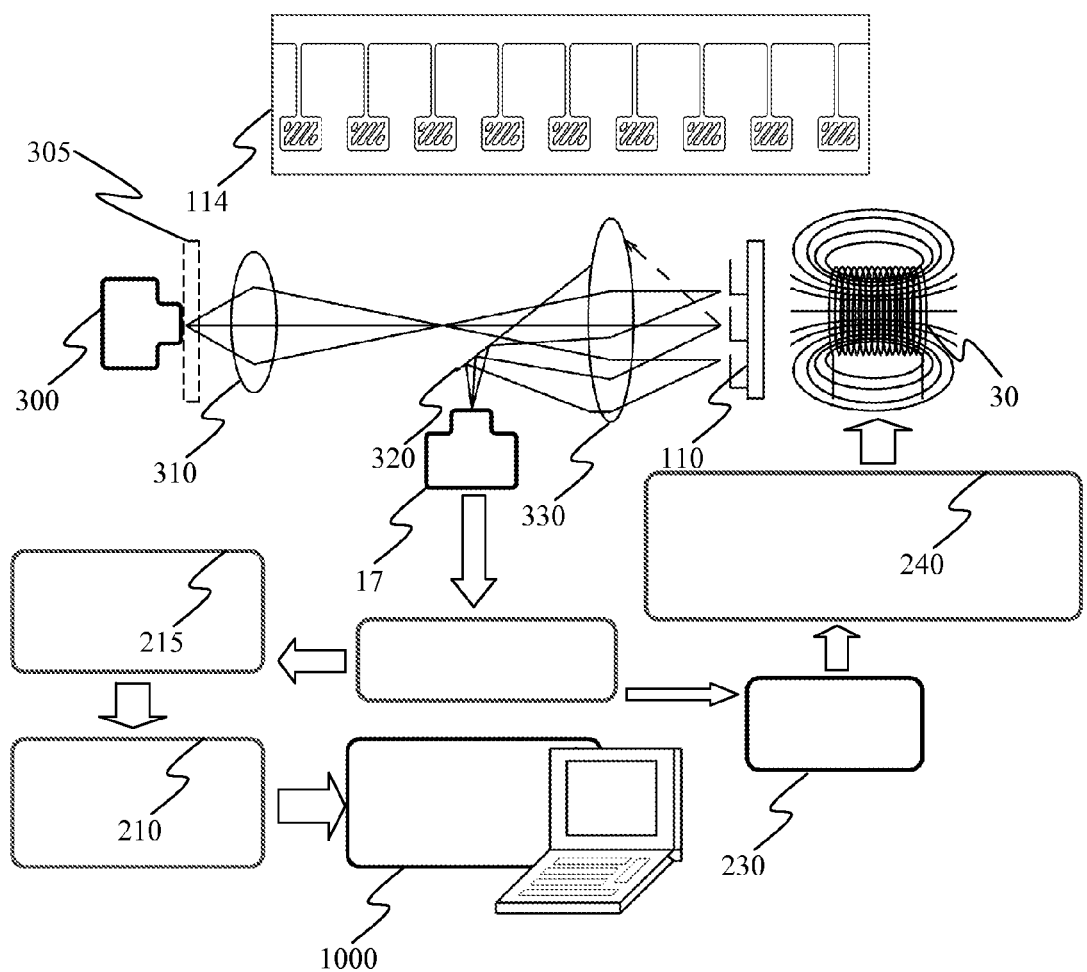
FIG. 16 is a diagrammatic view of a preferred embodiment of the optical readout and closed-loop electronics control system for parallel array readout.

FIG. 11-14 show a preferred embodiment hybrid staking where the MEMS sensor array 110 and the optoelectronics readout 15 are coupled to a device. Specifically, in this preferred embodiment, the MEMS sensor array 110 includes a substrate 118, preferably made of Si, having a via 119 aligning with each grating 116 of a cantilever 115 coupled to the substrate 118 and, at least one photodetector 17 coupled to substrate 118 such that refracted orders, preferably the $0^{th}$ refracted order 304 and $1^{st}$ refracted order 306 shown here, of laser 300 light can be detected (hereinafter called a "MEMS optoelectronics chip" (also sometimes called a "MEMS Chip and Optoelectronics chip). Most preferably, the via and photodetectors have protective layer 121 which is transparent and preferably a thin silicon dioxide or glass layer. While any laser source may be used, in this preferred embodiment, a VCSEL is chosen as the laser 300 source and flipchip bonded to the MEMS sensor array 110 such that the laser light may pass through the via 119. Additionally in this preferred embodiment, an electromagnet activation chip including an electromagnet 30 created on a silicon on insulator (SOI) layer 122 is coupled to the MEMS optoelectronics chip either permanently or preferably using removable coupling devices such as mechanical guides so that the electromagnet activation chip may activate cantilever of MEMS optoelectronics chip to detect fluids and moieties in fluids. As shown in the preferred embodiment in FIG. 15, the via 119 may be made into an array 1119 where a number of light sources may be used; for example, a single laser may be used for the vias 119 of the entire via array 1119, a single laser may be used create an array of laser beams; for example using a diffractive optical element 305 (see FIG. 16 below), or may be used for each via such as a VCSEL.

in preferred embodiment shown in FIG. 16, the DOE is a diffractive optical element 305 that can create an array of laser beams (i.e., fan-out grating). FIG. 16 is similar FIG. 4 but further preferably includes a band pass filter 215 and a display unit 1000.

Figure 17:
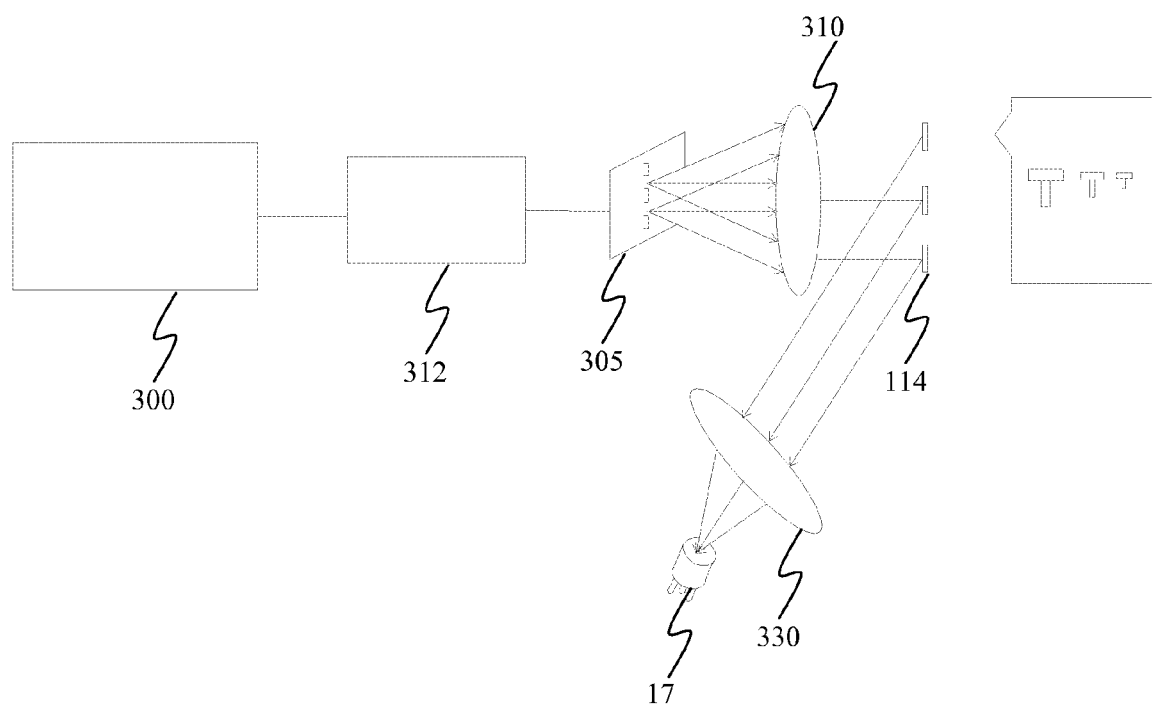
FIG. 17 is a diagrammatic view of a preferred embodiment of a readout method illustrating closed-loop controlled actuation with single coil and real-time monitoring of 2 cantilevers with single photodetector.
Figure 18:
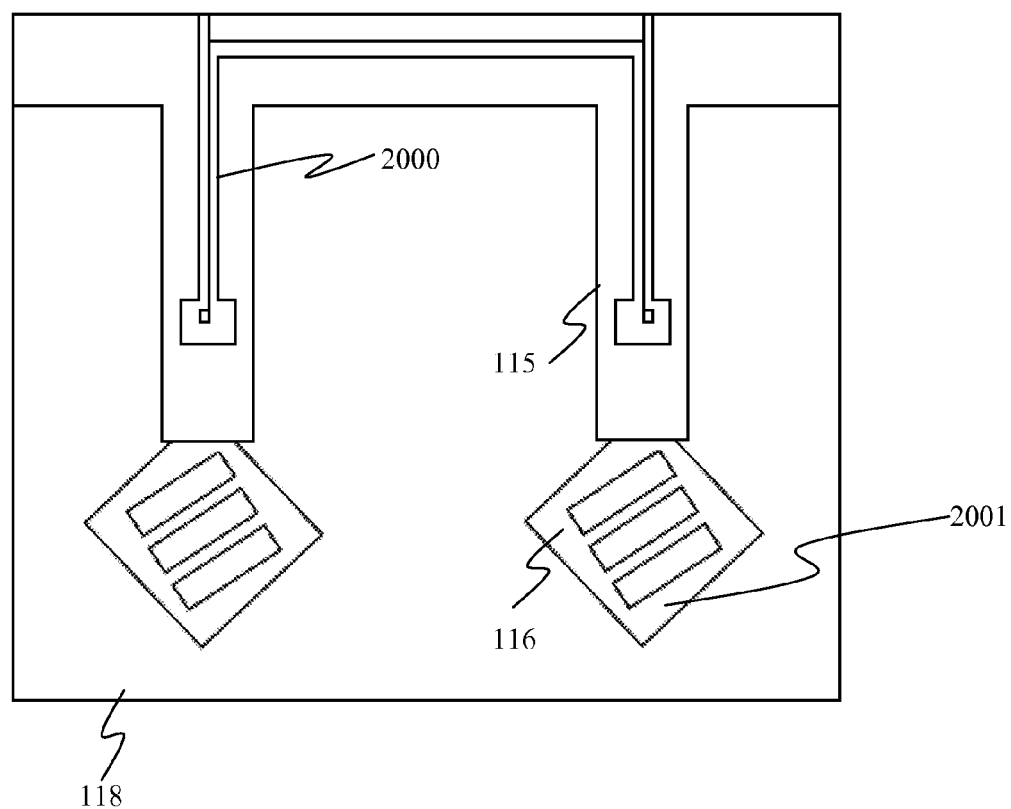
FIG. 18 is a diagrammatic view of a preferred embodiment of process layers for cantilever array with embedded diffraction gratins, sensing layer, and local microheaters for the invention.
Figure 19:
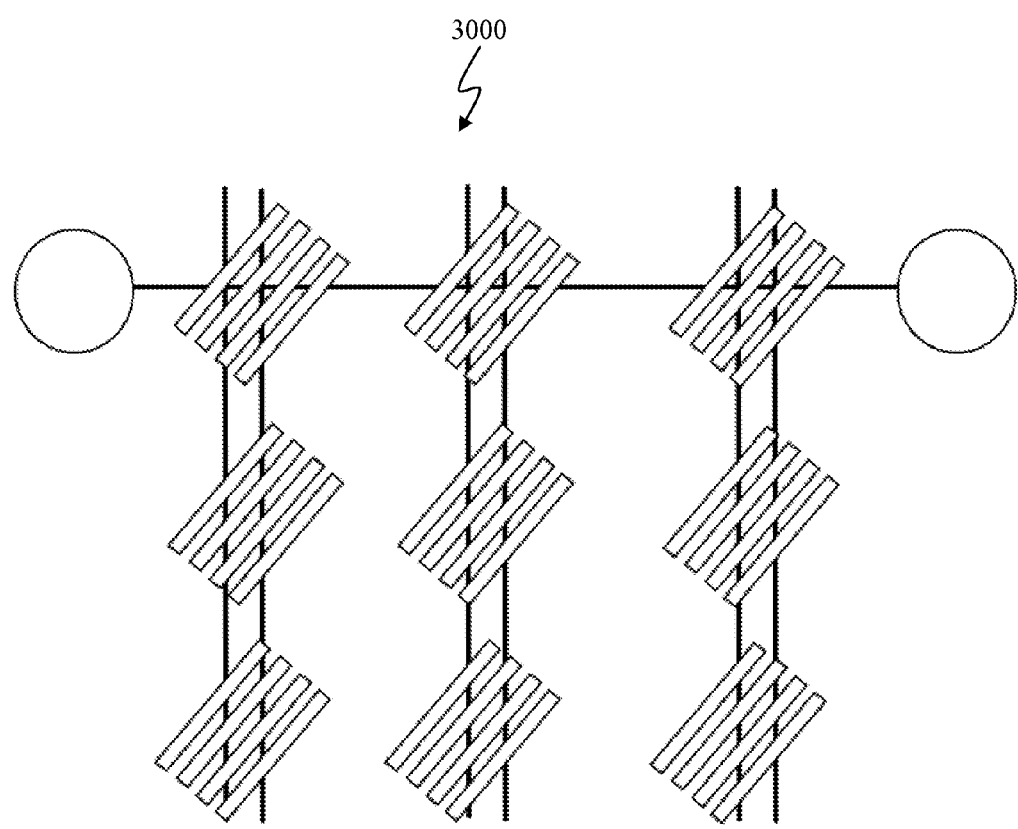
FIG. 19 is a diagrammatic view of a preferred embodiment illustrating the magnetic actuation of the thin film using a microcoil fabricated underneath the magnetic material.

In the preferred embodiment shown in FIG. 17, optical readout is not integrated with MEMS sensor and uses more conventional optical elements such as to lenses and diffraction gratings to direct the light beam reflected from the MEMS cantilevers onto a single photodetector that is placed at the Fourier plane. While not required, more preferably the laser 300 light is expanded using a beam expander 312 which couples to a diffractive optical element 305 before passing though conventional lens such as a first lens 310 to the sensor array 110 with refracted order passing though conventional lens such as a second lens 330 to the photodetector (PD) 17. Experimental results performed both in air and liquid for a preferred embodiment where 9 resonant cantilevers are monitored using a single photodetector using the setup illustrated in this figure.

the preferred embodiment shown in FIG. 19 includes embedding microheaters 2000 in the cantilever structure allows for local-heating on the cantilevers. This can be especially important for analyzing chemicals and biological samples as each reagent can have different adsorption and desorption rates at different temperatures. This can be used to improve specificity (or selectivity) of detection against different chemical and biological binding events. Localized heating can be to create temperature dependent spectra, DNA melting curves, and to increase specificity by introducing multi-modal detection capability. Nanostructured surface coatings 2001 can be used to increase the specificity/ preferably the activating means may include both a permanent magnet and an electromagnet fields to enhance the deflection of cantilevers at resonance. More preferably, the permanent magnet is generated by direct current (DC) and electromagnet is generated an alternating current (AC) to produce activating means. Preferably the orientation of the external magnet effects the magnetization of the cantilevers. Most preferably it is possible to use permanent or electromagnets premagnetized cantilevers to make the sensor more sensitive and more efficient (work with less energy).

In the preferred embodiment shown in FIG. 19 the coil is in the shape of a diffraction grating to facilitate optical readout as well as magnetic actuation. Alternatively, another preferred embodiment may include the magnetic material is fixed and coil can be moving. The magnetic coil is shaped such that it provides magnetic force for actuation and it serves as a diffraction grating for optical readout. If a scanning laser is preferably used as in FIG. 16, serial readout can be performed. More preferably, the cantilever can be actuated by energizing the magnetic coil Magnetic coils can be uses both as sensors and actuators. Preferably a coil can be the heater on or under the microcantilever; more preferably the coil can be on the moving or the static part; and most preferably heater and coil and diffraction grating can be combined together on the moving part or the static part.

Experiment Using
Mems Biosensor for Parallel and Highly Sensitive and Specific Detection of Hepatitis A label-free biosensor array that offers highly sensitive, high-dynamic-range and highly specific detection of Hepatitis A antigen is reported. Sensor array consists of Ni cantilevers with surfaces functionalized with Hepatitis A antibody.

Cantilevers are self-actuated at resonance using a single electromagnetic drive coil. Detection of resonance frequency is optical and facilitated by diffraction gratings embedded on cantilevers. All antibody-antigen interactions take place within undiluted bovine serum providing a high background noise due to unspecific molecules. A minimum detection limit of less than 0.1 ng/ml target molecule concentration is demonstrated. A high dynamic range is achieved, which is greater than 1000:1 concentration range. The proposed sensor array is shown to be compatible with most of the requirements of a hand-held biosensor including label-free, robust and real-time measurement with well integrated components.

INTRODUCTION

The preferred embodiment is a label-free biosensor system with integrated sensor, actuator, electronics, and fluidics flow cell that offer greatly improved sensitivity for the detection of biological molecules in undiluted bovine serum by utilizing dynamic-mode operation with no dip & dry process. The biosensor array is based on resonant MEMS cantilevers. We report for the first time better than 0.1 ng/ml sensitivity with >1000:1 dynamic range and high selectivity for Hepatitis A antibody-antigen interactions in serum.

Experimental Setup

In this preferred embodiment of the package housing includes i) a flowcell of less than 1 ml sample volume, ii) a MEMS chip with a vast number of cantilevers, and iii) an electrocoil as an actuation means. Preferably, detection is carried out through external optics. In this preferred embodiment an array of eight parallel cantilevers (vibrating mechanical structures) used with a diffraction grating fabricated at the tip of each cantilever. Preferably, each cantilever has a 2 to 3-m-wide slits embedded at the tip to form a grating interferometer between the vibrating mechanical structure and the bottom substrate. The use of the flowcell in this preferred embodiment is observed to improve sensitivity and selectivity results by avoiding drawbacks of the "dip & dry" method.

In this preferred embodiment, microfabrication can be a simple one-mask process. The only lithography step is needed during the definition of cantilevers with integrated diffraction gratings. More preferably, fabrication is carried out on a 4" <100> Si wafer. Preferably, cantilevers are made of electroplated Nickel with a thin Au layer underneath, but could be made of other suitable materials. To prepare the cantilever of this preferred method, Au has a thickness of 100 nm and serves as i) seed layer during electroplating, and ii) functionalization platform for biosensing, and the timed etch of Au is important to ensure the presence of a Au layer underneath the cantilevers which can be verified by scanning electron microscopy by removing selected cantilevers from the chip and checking their backside for the presence of Au. In this preferred embodiment, electroplating is followed by a final release in KOH to a depth of around 10 m.

In this preferred embodiment a laser diode 300 is used as the wavesource for the diffractive readout. Preferably, the laser 300 is focused on the cantilevers 114 through a transparent window machined on the flowcell, a Si surface formed after KOH etch serves as the reference surface for diffraction, a Ni surface on the grating platform is the movable surface whose frequency is to be monitored. In this preferred embodiment, a photodetector is placed at one of the diffraction orders 302 and the obtained signal is at the same frequency with the resonant oscillations. More preferably, a frequency counter is added to the setup that provides an improved way to average millions of cycles within a few seconds which allows sub-Hz frequency sensitivity even when the cantilevers are actuated in liquids. Most preferably, the feedback control loop is self-starting by using the thermal vibrations/Brownian motion and allows measurement results within 10 to 20 sec. Preferably, compensator electronics can be used to cancel the inductive effects for a broad range of frequencies which increased the coil current more than 30 times.

Biological Measurements

After a standard RCA-1 clean, sensor array chips are placed within the flowcell. Au surface on the cantilevers is functionalized with Hepatitis A antibodies. Dithiobis (succinimidyl propionate) (DSP) crosslinker is used for this purpose and the binding sites are saturated with antibodies dissolved in dimethyl sulfoxide (DMSO) solution using the flow cell.

After functionalization, chips are exposed to different concentrations of Hepatitis A and Hepatitis C antigens in undiluted bovine serological complex (serum). Concentrations of 0.04, 0.1, 1, 10, 100 ng/ml are utilized for each case. Hepatitis C antigen is mixed in bovine serum in increasing concentrations and introduced to the chip containing Hepatitis A antibody. These measurements serve as negative controls. Subsequently, each chip is subjected to the correct antigens at increasing concentrations until sensor response is almost saturated.

Reference measurements have to be taken in a phosphate-buffered saline (PBS) solution before the injection of the serum with antigens. Chips are similarly washed with PBS after exposure to target molecules and measurements are repeated in PBS. The difference between these two measurements is taken as the frequency shift of interest.

Measurements are taken at different concentration levels and using 10-16 different cantilevers for each chip by using 2 chips and following the protocol in Table 1. Relative frequency shift measurement variations between cantilevers are smaller than 10%. Results and statistical data are presented in Tables 2 and 3.

TABLE 1

Experimental protocol applied to biosensors chip1 and chip 2.

| Biosensor Chip 1 | | Biosensor Chip 2 | |
|---|---|---|---|
| Process | Concentration | Process | Concentration |
| DSP Cross linker | 2 mM | DSP Cross linker | 2 mM |
| Hepatitis A Antibody | ~1000 ng/ml | Hepatitis C Antibody | ~1000 ng/ml |
| Bovine Serum | Undiluted | Bovine Serum | Undiluted |
| Negative Control Hepatitis C Antigen (ng/ml) | 0.04 | Negative Control Hepatitis A Antigen (ng/ml) | 0.04 |
| | 0.1 | | 0.1 |
| | 1 | | 1 |
| | 10 | | 10 |
| | 100 | | 100 |
| Positive Control Hepatitis A Antigen (ng/ml) | 0.04 | Positive Control Hepatitis C Antigen (ng/ml) | 0.04 |
| | 0.1 | | 0.1 |
| | 1 | | 1 |
| | 10 | | 10 |
| | 100 | | 100 |

TABLE 2

Results of Negative Control Experiments for Selectivity

| Concentration | Hep A Ab & Hep C Ag | | Hep C Ab & Hep A Ag | |
|---|---|---|---|---|
| [ng/ml] | [ppm] | [ppm] | [ppm] | [ppm] |
| 0.04 | 6.90 | 0.29 | 6.93 | 0.13 |
| 0.10 | 6.89 | 0.49 | 6.37 | 0.14 |

TABLE 2-continued

Results of Negative Control Experiments for Selectivity

| Concentration | Hep A Ab & Hep C Ag | | Hep C Ab & Hep A Ag | |
|---|---|---|---|---|
| [ng/ml] | [ppm] | [ppm] | [ppm] | [ppm] |
| 1 | 6.74 | 0.55 | 7.45 | 0.12 |
| 10 | 6.58 | 1.73 | 6.67 | 0.13 |
| 100 | 6.89 | 0.23 | 7.11 | 0.15 |

TABLE 3

Results of Control Experiments for Sensitivity and Repeatibility

| Concentration | Hep A Ab & Ag Exp 1 | | Hep A Ab & Ag Exp 2 | | Hep C Ab & Ag | |
|---|---|---|---|---|---|---|
| [ng/ml] | [ppm] | [ppm] | [ppm] | [ppm] | [ppm] | [ppm] |
| 0.04 | 8.89 | 1.16 | 5.47 | 2.45 | 9.80 | 0.15 |
| 0.10 | 20.01 | 1.08 | 20.52 | 2.45 | 26.01 | 7.95 |
| 1 | 202.86 | 16.71 | 195.51 | 14.92 | 275.00 | 55.80 |
| 10 | 1917.78 | 37.82 | 1975.92 | 58.20 | 2410.00 | 489.00 |
| 100 | 3029.12 | 94.42 | 3147.07 | 406.43 | 3600.00 | 590.00 |

Ab: antibody and Ag: antigen. The mean value (m) and standard deviation (s) of relative resonant frequency shift in units of parts per million (ppm) for 11 cantilevers (15 cantilevers for exp 1 only) monitored during the experiments.

The following observations can be made on Table 2 and Table 3:

i) Variations among measurements are so small. Details can be seen in Tables 2 and 3 show small deviation around the mean values with a noise level is around 7 ppm.

ii) Negative control experiments give nearly constant results irrespective of the concentration, i.e. the response of MEMS chip functionalized with Hepatitis A antibody to Hepatitis C antigen is nearly constant irrespective of Hepatitis C concentration.

iii) Actual measurement chips, where Hepatitis A antibody is exposed to Hepatitis A antigen provide a linear response up to about 100 ng/ml concentration without saturation.

As a result one can conclude that the proposed platform is a candidate for highly selective and sensitive MEMS biosensor. Since its immunity to environmental noise can be accomplished, it can be in principle used as a hand-held device in the field.

CONCLUSION

Electromagnetically driven Ni cantilevers in a MEMS biosensor platform have been shown. A package incorporating an electrocoil actuator, a flowcell and the MEMS chip is introduced along with a feedback mechanism facilitating the use of the resonant technique in serum. All measurements are carried out in liquid.

Hepatitis is chosen as the targeted disease for the biosensor. Results obtained with Hepatitis sensing are presented. It is observed that the proposed measurement principle provides consistent data on Hepatitis antibody-antigen interactions in the presence of high background noise due to the use of bovine serum.

A minimum detectable concentration of 0.1 ng/ml is obtained which is comparable to the labeled sensing methods such as ELISA.

Measurements are performed up to 100 ng/ml, which provides 1000:1 dynamic range.

The preferred system provides a reliable means of highly selective and sensitive biosensing, which is also label-free and real-time. In addition, the ability for parallel measurement is also expected from an ideal biosensor. Parallelism is strongly in line with capabilities of microfabrication and can easily be incorporated if accompanied by a suitable method of functionalization. The ability of the proposed technique for multiplexing can also be demonstrated. A total of nine cantilevers can be monitored through a single photodiode. To be useful for parallel measurements, multiplexing should be combined with an appropriate functionalization technique that can address individual cantilevers and functionalize them with different biologically active coatings.

Overall this sensor array system is label-free, robust, real-time and well integrated. It can be made portable and disposable, and seems very promising for point of care diagnostics and drug discovery applications.

The preferred embodiment of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. An apparatus for sensing dynamic changes such as mass or viscosity comprising:
    a disposable cartridge having at least one micro-electromechanical sensor;
    at least one light source coupled to the at least one micro-electromechanical sensor;
    at least one photodetector coupled to the at least one micro-electromechanical sensor and the light source; and
    a control electronics coupled to at least one actuation means;
    wherein the at least one actuation means can be removably coupled to the at least one micro-electromechanical sensor and
    wherein the control electronics and user interface can be removably coupled to the at least one photodetector.

2. The apparatus according to claim 1, wherein the at least one light source is a single laser source and wherein the at least one photodetector is a single photodetector.

3. The apparatus according to claim 1, wherein the at least one micro-electromechanical sensor comprises at least one vibrating structure for sensing and an interference means coupled with each vibrating mechanical structure.

4. The apparatus according to claim 1, wherein the at least one micro-electromechanical sensor comprises at least one vibrating structure for sensing and an interference means coupled with at least one vibrating mechanical structure and a substrate having a via for each mechanical structure to allow the light source to pass through the substrate to the mechanical structure.

5. The apparatus according to claim 4, wherein the photodetector is located on the substrate.

6. The apparatus according to claim 5, wherein the light source is coupled to the substrate.

7. The apparatus according to claim 5, further comprising at least one heating element for each vibrating mechanical structure.

8. The apparatus according to claim 1, wherein the micromechanical sensor comprises plurality of vibrating mechanical structures.

9. The apparatus according to claim 8, wherein the vibrating mechanical structures are arranged in a two-dimensional array.

10. The apparatus according to claim 4, wherein the at least one light source is a single light source that is scanned across each vibrating mechanical structure.

11. The apparatus according to claim 4, wherein the interference mean is a grating coupled to the each vibrating mechanical structure.

12. The apparatus according to claim 10, wherein the at least one light source is selected from the group consisting of laser diode, LED or VCSEL.

* * * * *